United States Patent [19]

Barnes, Sr. et al.

[11] Patent Number: 5,564,927
[45] Date of Patent: Oct. 15, 1996

[54] DENTURE APPARATUS

[75] Inventors: Larry W. Barnes, Sr.; David O. Snyder, both of Tulsa, Okla.

[73] Assignee: Sure-Bite, Inc., Tulsa, Okla.

[21] Appl. No.: 396,737

[22] Filed: Mar. 1, 1995

[51] Int. Cl.[6] ............................ A61C 13/12; A61C 13/225
[52] U.S. Cl. ............................................ 433/179; 433/169
[58] Field of Search ................................... 433/169, 170, 433/177, 179

[56] References Cited

U.S. PATENT DOCUMENTS

| | | |
|---|---|---|
| 452,653 | 5/1891 | Stedman . |
| 474,104 | 5/1892 | Stedman . |
| 1,242,989 | 10/1917 | Schreier . |
| 1,322,355 | 11/1919 | Schreier . |
| 1,473,673 | 11/1923 | Elsas . |
| 1,761,902 | 6/1930 | Anderson . |
| 2,252,935 | 8/1941 | Liedberg . |
| 2,309,084 | 1/1943 | Wintrebert . |
| 2,598,998 | 6/1952 | Kaplan . |
| 2,666,988 | 1/1954 | Myers . |
| 2,770,881 | 11/1956 | Lodi . |
| 3,043,005 | 7/1962 | Morris . |
| 3,362,072 | 1/1968 | Nowaczyk . |
| 3,495,332 | 2/1970 | Joseph . |
| 3,618,214 | 11/1971 | Armstrong .................. 433/19 |
| 5,286,198 | 2/1994 | Barnes .................. 433/179 |

*Primary Examiner*—Robert P. Swiatek
*Assistant Examiner*—Yvonne R. Abbott
*Attorney, Agent, or Firm*—Head, Johnson & Kachigian

[57] ABSTRACT

A denture apparatus which includes an upper denture and an opposed lower denture. At least one spring is enclosed and held within a spring enclosure assembly, the spring enclosure assembly attached only to the upper denture. The assembly is adapted to contact the lower denture when the dentures are brought in proximity with each other in order to urge the lower denture away from the upper denture, thereby retaining the dentures in proper position.

10 Claims, 1 Drawing Sheet

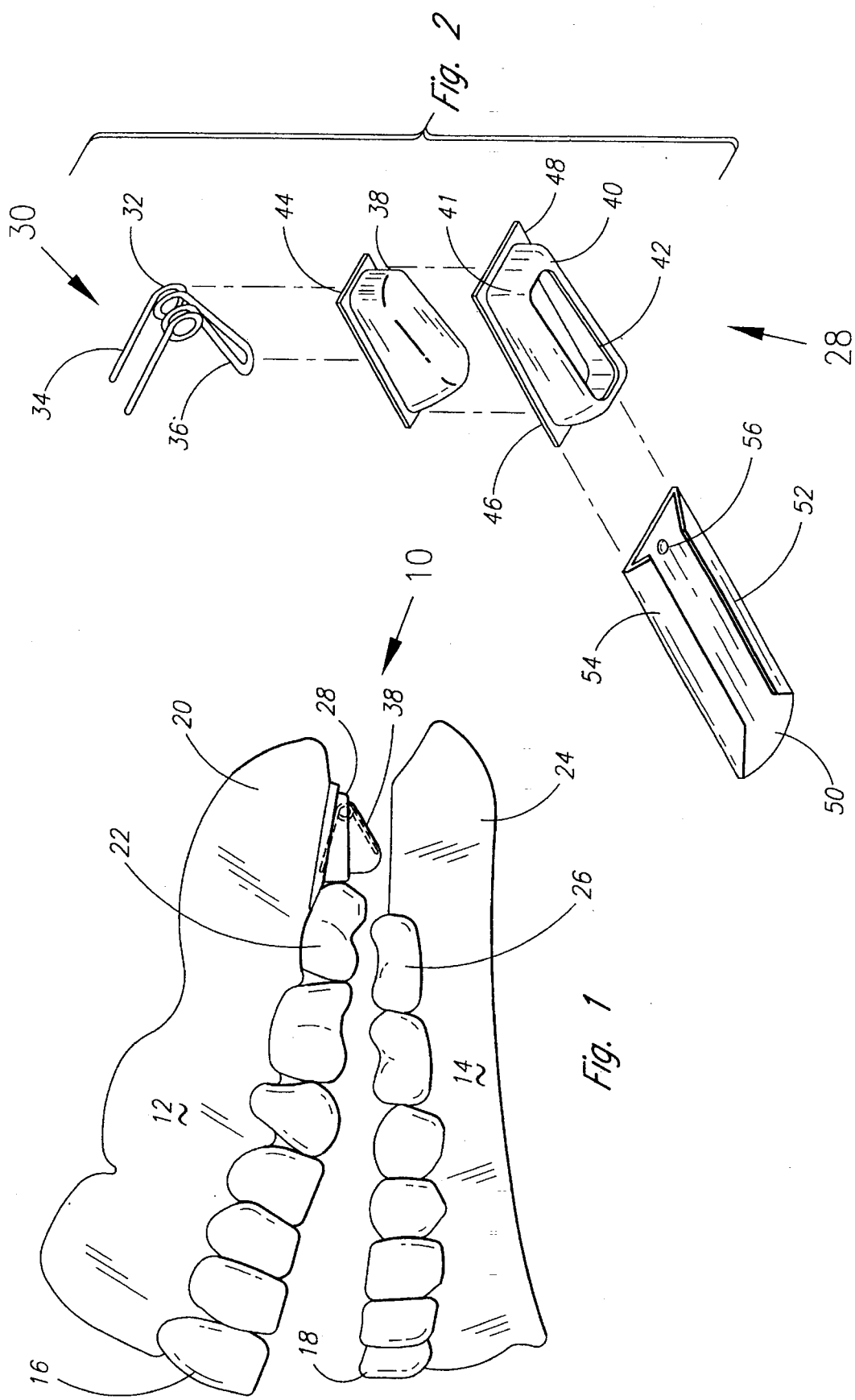

DENTURE APPARATUS

BACKGROUND OF THE INVENTION

1. Field of the Invention

The present invention is directed to a denture apparatus for removable dentures. In particular, the present invention is directed to a denture apparatus for removable dentures which will provide a force to urge the lower denture away from the upper denture in order to assist in retaining the dentures in proper position during eating.

2. Prior Art

In various instances, prosthodontic dentistry calls for the replacement of teeth with dentures. This may be called for in various instances including periodontal disease, decay or injury. Although it may be possible to surgically connect dentures to the jaw, removable dentures are often prescribed.

Where a full denture is utilized, the base of the upper denture normally covers the palate. The lower denture may be horseshoe-shaped to leave room for the tongue. A full denture is supported by the underlying gum and bone tissues of the dental ridge.

A lower denture is less stable than an upper denture. Moreover, it is known that a full denture can stand only very limited chewing pressure. When a denture wearer is eating with the dentures in place, the lower plate has a tendency to be displaced or flip up when the wearer is biting in the front or on the sides.

At least one estimate is that full dentures can only withstand one-tenth the chewing pressure of natural teeth.

Various provisions have been made in the past to affix or connect the upper denture to the lower denture. Examples of such approaches in Liedberg (U.S. Pat. No. 2,252,935), Anderson (U.S. Pat. No. 1,761,902) and Elsas (U.S. Pat. No. 1,473,673).

Morris (U.S. Pat. No. 3,043,005) discloses a dental anchoring system having a pair of leaf springs affixed to one of the plates to exert an anchoring separation of the plates.

One of the Applicants herein, Barnes (U.S. Pat. No. 5,286,198), has provided a denture apparatus with coil springs, each having an extending leg to engage the lower denture. By not connecting the lower to the upper denture, lateral and longitudinal movement of the dentures with respect to each other is allowed.

It is desirable to provide a denture apparatus to provide a force to urge the lower denture away from the upper denture with a spring which is removable from the denture apparatus.

Accordingly, it is a principal object and purpose of the present invention to provide a denture apparatus which will provide a force to retain and stabilize the position of the dentures during eating.

It is an additional object and purpose of the present invention to provide a denture apparatus having springs and spring enclosure assemblies that will not promote abrading or pinching of the mouth tissue.

It is an additional object and purpose of the present invention to provide upper and lower dentures that have full lateral and longitudinal movement with respect to each other.

SUMMARY OF THE INVENTION

The present invention is directed to a denture apparatus which includes a maxillary or upper denture and an opposed mandibular or lower denture, each of which have corresponding teeth.

The upper denture includes a right molar pad and a left molar pad located behind or posterior to the last permanent molars.

Likewise, the lower denture includes a right molar pad and a left molar pad located posterior to or behind the last molars.

A spring and a spring enclosure assembly extend outward from the upper left molar toward the lower left molar. Additionally, a spring and a spring assembly extend outward from the upper right molar pad toward the lower right molar pad.

The spring is a coil spring which includes a coil and a pair of legs which extend radially therefrom. The spring is not permanently connected or attached to the spring enclosure assembly or to the molars. Rather, the spring is received and fits within a cover which provides an enclosure except for an opening on one side. The spring maintains the cover under tension at all times. When the upper denture and lower denture are brought together, the enclosure cover which is under tension will engage with the lower left molar pad. Accordingly, the cover of the spring enclosure assembly urges the lower denture away from the upper denture. This denture separating force will counteract the force developed from eating with the front teeth.

The spring enclosure assembly includes a holder having a receptacle and a central opening in the receptacle. The receptacle is slightly larger than the area of the cover so that the cover may be received in the holder.

The cover includes an extending edge which extends near the opening of the cover. The extending edge is slightly smaller in area than the receptacle so that it is received in the receptacle. The extending edge is slightly larger than the area of the central opening of the holder. Thus, while the cover will extend into the central opening, it will not be allowed to pass therethrough.

The cover will be allowed to move within the receptacle of the holder in response to tension from the spring and in response to engagement with the lower molar.

A mechanism is provided to attach the spring enclosure assembly to the upper denture and to remove the spring enclosure assembly from the upper denture. The holder has a pair of opposed extending lips which are slidably received in a flat base track having a pair of opposed edges. The spring, cover and holder may be attached to the upper denture by sliding the holder into the base track.

BRIEF DESCRIPTION OF THE DRAWINGS

FIG. 1 illustrates a side view of a denture apparatus constructed in accordance with the present invention; and FIG. 2 illustrates an exploded view apart from the dentures of the present invention as shown in FIG. 1.

DETAILED DESCRIPTION OF THE PREFERRED EMBODIMENTS

Referring to the drawings in detail, FIG. 1 illustrates a side view of a denture apparatus 10 constructed in accordance with the present invention. The denture apparatus 10 includes a maxillary or upper denture 12 and an opposed mandibular or lower denture 14. The dentures 12 and 14 are vertically aligned with each other. The maxillary and mandibular dentures have corresponding teeth 16 and 18, respectively.

The upper maxillary denture and lower mandibular denture are used as replacements for natural teeth and are supported by the underlying gum and bone tissues of the dental ridge of the patient (not shown). When a denture wearer eats with the front teeth, the upper denture and the lower denture are brought together under force. A leverage force is created which may dislodge the positioning of the dentures and, in particular, dislodge the rearmost portion of the dentures.

The upper denture 12 includes a right molar pad (not visible in FIG. 1) and a left molar pad 20 located behind or posterior to the last molars. Only the upper left molar pad is visible in FIG. 1. The upper molar pads or maxillary tuberosity are posterior or distal to the last permanent molar 22.

Likewise, the lower denture 14 includes a right molar pad (not visible in FIG. 1) and a left molar pad 24 which is located posterior to or behind the last molar 26. Only the lower left molar pad 24 is visible in FIG. 1. The lower molar pad or mandibular retromolar pad is a recognized anatomical structure which is posterior or distal to the last molar 26 just in front of the ascending ramus of the mandible.

As will be described in detail herein, a spring and a spring enclosure assembly 28 extend outward from the upper left molar pad 20 toward the lower left molar pad 24.

FIG. 2 is an exploded view of a spring 30 and the spring enclosure assembly 28 removed and apart from the upper denture 12.

In the present embodiment, the spring 30 is a coil spring which includes a coil 32 and a pair of legs 34 and 36 which extend radially therefrom. The legs 34 and 36 are a part of and extend from the coil portion 32 so that the legs are at all times under tension.

The spring 30 is not permanently connected or attached to the spring enclosure assembly 28 or to the molars. Rather, the spring 30 is received and fits within a cover 38 which provides an enclosure except for an opening on one side (the opening not visible in FIG. 2). The spring 30 thus maintains the cover 38 to be under tension at all times.

When the mouth is relaxed, there is a small freeway space between the teeth of 3–4 mm when the jaw is relaxed. When the upper denture 12 and the lower denture 14 are brought together, such as occurs during eating and chewing, the enclosure cover 38 will engage with the lower left molar pad 24. The cover 38 will engage with the lower molar pad prior to the upper and lower teeth being brought together. Accordingly, the cover 38 of the spring enclosure assembly 28 urges the lower denture 14 away from the upper denture 12. This denture separating force will counteract the force developed from eating with the front teeth. Accordingly, the present invention acts to stabilize the dentures.

It will be appreciated from FIG. 1 that the cover 38 is in angular relation to the lower denture 14.

The spring enclosure assembly 28 includes a holder 40 having a receptacle 41 and a central opening 42. The receptacle is slightly larger than the cover so that the cover is received in the holder. The cover 38 includes an extending edge 44 which extends near the opening of the cover. The extending edge is slightly smaller in area than the receptacle so that it is received in the receptacle. The edge 44 of the cover is larger than the area of the central opening 42 of the holder. While the cover 38, thus, will extend into the central opening 42, it will not be allowed to pass therethrough.

The cover 38 will, thus, be allowed to move within the receptacle of the holder 40 in response to tension from the spring 30 and in response to engagement with the lower molar. The cover 38 will normally be in the position shown in FIG. 1 until it comes into contact with the lower molar. Under force from the lower molar, the cover retracts into the holder.

While a wear plate, such as employed in Barnes U.S. Pat. No. 5,286,198, might be used, it has not been found necessary in the present embodiment.

A mechanism is provided to attach the spring enclosure assembly 28 to the upper denture 12 and to remove the spring enclosure assembly 28 from the upper denture. The holder 40 has a pair of opposed extending lips 46 and 48. The lips of the holder are slidably received in a flat base track 50. The base track includes a pair of opposed edges 52 and 54.

The base track may also optionally include a dimple 56 which extends slightly above the level of the base track. Under slight force, the holder 40 may be inserted past the dimple 56 which will discourage the holder from being removed unless sufficient force is provided to move the holder over the dimple.

The spring enclosure assembly and the spring might alternately be designed to extend from the lower denture 14 toward the upper denture 12, although it has been found that the present arrangement is preferable to avoid in interfering with the tongue.

The foregoing description has been relegated to the upper left molar pad and the lower left molar pad of the dentures. It is contemplated that a similar coil spring would be received within a similar spring enclosure assembly held in a similar flat base on the upper right molar pad which would then engage the lower right molar pad (not visible in FIG. 1).

The spring enclosure assembly assures that the coil spring will not be exposed. Accordingly, the design will avoid allowing food to build up in and around the spring. Additionally, the spring discourages any abrading or pinching of the mouth tissue by the spring since it is completely enclosed.

Moreover, in the unlikely event that a spring should break, it will nonetheless remain within the holder.

Finally, it will be understood that the springs in the present invention are replaceable so that the force may be varied by inserting a different spring.

The base 50 may be added or affixed to existing dentures. Alternatively, the base 50 may be fabricated as part of the dentures during their manufacture.

To produce a denture apparatus in accordance with the present invention, initially an upper and a lower denture is manufactured in a mold. A flat base 50 may be embedded into the upper denture wherein the flat base includes a track having the proposed edges 52 and 54. A coil spring is inserted into the cover 38 following which the cover is inserted into the receptacle in the holder. The receptacle will reside in a central opening in the holder but will not pass through the holder because of the edge 44 on the cover. The spring, cover and holder are then attached to the upper denture by sliding the holder into the base track between the opposed edges.

To remove the spring, cover and holder from the dentures, the reverse procedure is performed.

While the invention herein has been described with relation to full dentures, it will be understood that the invention may also be utilized with partial dentures as well.

Whereas, the present invention has been described in relation to the drawings attached hereto, it should be understood that other and further modifications, apart from those shown or suggested herein, may be made within the spirit and scope of this invention.

What is claimed is:

1. A denture apparatus which comprises:
   (a) an upper denture;
   (b) an opposed lower denture;
   (c) at least one spring means; and
   (d) a depressible cover for said at least one spring means, said cover retained within a holder attached only to said upper denture, wherein said cover is adapted to contact said lower denture when said dentures are brought in proximity with each other in order to urge said lower denture away from said upper denture.

2. A denture apparatus as set forth in claim 1 wherein said upper denture includes a right molar pad and a left molar pad and including one said spring means, one said cover and one said holder for said right molar pad and one said spring means, one said cover and one said holder for said left molar pad.

3. A denture apparatus as set forth in claim 1 wherein said at least one spring means includes a coil at least one spring.

4. A denture apparatus as set forth in claim 1 wherein said holder has a receptacle having a central opening for receiving said cover therein and wherein said cover includes an extending edge larger than said central opening to prevent said cover from being removed from said holder.

5. A denture apparatus as set forth in claim 1 wherein said holder is removably attached to said upper denture.

6. A denture apparatus as set forth in claim 5 wherein said holder has extending lips which may be slidably received in a flat base track.

7. A denture apparatus having an upper denture and an opposed lower denture, which apparatus comprises:
   (a) at least one spring means;
   (b) a spring enclosure assembly to hold and enclose said at least one spring means including a spring cover to receive said spring means and a holder having a receptacle, said holder receptacle having a central opening wherein said spring cover is received in said receptacle and said central opening; and
   (c) means to insert and attach said assembly to said upper denture for use and to remove said assembly from said upper denture after use.

8. A denture apparatus as set forth in claim 7 wherein said upper denture includes a right molar pad and a left molar pad and including one said spring means and one said enclosure assembly for said right molar pad and one said spring means and enclosure assembly for said left molar pad.

9. A denture apparatus as set forth in claim 7 wherein said at least one spring means includes a coil at least one spring.

10. A process to produce a denture apparatus having an upper denture and an opposed lower denture, which process comprises:

preparing said upper and lower dentures from a mold;

embedding a flat base having a track in said upper denture;

inserting a spring into a cover having an extending edge and inserting said cover into a holder through a central opening in said holder; and attaching said spring, said cover and said holder to said upper denture by sliding said holder in said base track.

* * * * *